US009230354B2

(12) United States Patent
O'Connor et al.

(10) Patent No.: US 9,230,354 B2
(45) Date of Patent: Jan. 5, 2016

(54) SYSTEM AND METHOD FOR MOLECULAR BREAST IMAGING ENERGY SPECTRUM IMAGING AND ANALYSIS

(75) Inventors: Michael K. O'Connor, Rochester, MN (US); Amanda Weinmann, Inver Grove Heights, MN (US)

(73) Assignee: Mayo Foundation for Medical Education and Research, Rochester, MN (US)

( * ) Notice: Subject to any disclaimer, the term of this patent is extended or adjusted under 35 U.S.C. 154(b) by 254 days.

(21) Appl. No.: 13/882,404

(22) PCT Filed: Oct. 31, 2011

(86) PCT No.: PCT/US2011/058581
§ 371 (c)(1),
(2), (4) Date: Apr. 29, 2013

(87) PCT Pub. No.: WO2012/058670
PCT Pub. Date: May 3, 2012

(65) Prior Publication Data
US 2013/0216113 A1   Aug. 22, 2013

Related U.S. Application Data

(60) Provisional application No. 61/408,301, filed on Oct. 29, 2010.

(51) Int. Cl.
*G06T 11/60* (2006.01)
*A61B 6/00* (2006.01)
(52) U.S. Cl.
CPC .............. *G06T 11/60* (2013.01); *A61B 6/4258* (2013.01); *A61B 6/482* (2013.01); *A61B 6/502* (2013.01); *A61B 6/5235* (2013.01)

(58) Field of Classification Search
None
See application file for complete search history.

(56) References Cited

U.S. PATENT DOCUMENTS 3,955,088 A * 5/1976 Muehllehner et al. ... 250/363.03
4,873,632 A * 10/1989 Logan et al. ............. 250/363.02
4,899,054 A * 2/1990 Barfod ..................... 250/369
(Continued)

FOREIGN PATENT DOCUMENTS

CN            101847257 A  *  9/2010

OTHER PUBLICATIONS

The International Search Report and Written Opinion as mailed on Mar. 2, 2012 for International Application No. PCT/EP2011/058581.

*Primary Examiner* — Tsung-Yin Tsai
(74) *Attorney, Agent, or Firm* — Yakov Sidorin; Quarles & Brady LLP

(57) ABSTRACT

A system and method is provided for imaging a region of interest ("ROI") including a breast having received a reduced dose of radionuclide using an imaging system including at least two gamma detectors. The acquired imaging data is analyzed respect to an energy characteristic and divided into subsets of data based on the analysis. A plurality of images is generated using the subsets of data, wherein the plurality of images include a primary image corresponding to subsets of data having energy including the energy characteristic and multiple secondary images corresponding to subsets of data having energy not including the energy characteristic. Each of the plurality of images is processed using energy information associated with each of the plurality of images and the processed plurality of images is combined to form a composite image of the ROI.

20 Claims, 5 Drawing Sheets

(56) References Cited

U.S. PATENT DOCUMENTS

| | | | |
|---|---|---|---|
| 5,371,672 A * | 12/1994 | Motomura et al. | 600/431 |
| 8,362,434 B2 | 1/2013 | O'Connor et al. | |
| 2002/0143249 A1 * | 10/2002 | Tornai et al. | 600/425 |
| 2003/0013950 A1 | 1/2003 | Rollo et al. | |
| 2003/0076988 A1 * | 4/2003 | Liang et al. | 382/131 |
| 2005/0259889 A1 | 11/2005 | Ferrari et al. | |
| 2008/0224050 A1 * | 9/2008 | Thielemans et al. | 250/362 |
| 2008/0253640 A1 | 10/2008 | Gagnon et al. | |
| 2008/0277587 A1 | 11/2008 | Case et al. | |
| 2010/0034734 A1 | 2/2010 | O'Connor et al. | |
| 2010/0104505 A1 | 4/2010 | O'Connor | |
| 2011/0248174 A1 | 10/2011 | O'Connor et al. | |
| 2011/0286651 A1 * | 11/2011 | Yu et al. | 382/131 |

* cited by examiner

SYSTEM AND METHOD FOR MOLECULAR BREAST IMAGING ENERGY SPECTRUM IMAGING AND ANALYSIS

CROSS-REFERENCE TO RELATED APPLICATIONS

This application represents the national stage entry of PCT International Application No. PCT/US2011/058581 on Oct. 31, 2011 and claims the benefit of U.S. Provisional Patent Application No. 61/408,301 filed Oct. 29, 2010. The contents of both of these applications are hereby incorporated by reference as if set forth in their entirety herein.

STATEMENT REGARDING FEDERALLY SPONSORED RESEARCH

No funding information

FIELD OF THE INVENTION

The present invention relates to a method for imaging a region of interest using an imaging system including at least two gamma detectors. Specifically, the present invention relates to a system method for imaging a breast using a molecular breast imaging system and an increased spectrum analysis over traditional systems and methods.

BACKGROUND OF THE INVENTION

Screening mammography has been the gold standard for breast cancer detection for over 30 years. However, the sensitivity of screening mammography varies considerably. The most important factor in the failure of mammography to detect breast cancer is radiographic breast density. In studies examining the sensitivity of mammography as a function of breast density, it has been determined that the sensitivity of mammography falls from 87-97 percent in women with fatty breasts to 48-63 percent in women with extremely dense breasts.

Diagnostic alternatives to mammography include ultrasound and MRI. The effectiveness of whole-breast ultrasound as a screening technique does not appear to be significantly different from mammography. MRI has a high sensitivity for the detection for breast cancer and is not affected by breast density. However, since bilateral breast MRI is currently approximately 20 times more expensive than mammography, it is not in widespread use as a screening technique.

Another prior-art technology is positron emission mammography (PEM). This uses two, small, opposing PET detectors to image the breast. The PEM technology offers excellent resolution; however, the currently available radiotracer (F-18 Fluoro deoxyglucose) requires that a patient fast overnight, the patient must have low blood levels (this is often a problem for diabetics), and after injection, the patient must wait 1-2 hours for optimum uptake of F-18FDG in the tumor. The high cost of these PET procedures coupled with the long patient preparation time reduces the usefulness of this procedure and makes it difficult to employ for routine breast evaluation.

Radionuclide imaging of the breast (scintimammography) with Tc-99m sestamibi was developed in the 1990s and has been the subject of considerable investigation over the last 10-15 years. This functional method is not dependent upon breast density. Large multi-center studies have shown the sensitivity and specificity of scintimammography in the detection of malignant breast tumors to be approximately 85 percent. However, these results only hold for large tumors and several studies have shown that the sensitivity falls significantly with tumor size. The reported sensitivity for lesions less than 10-15 mm in size was approximately 50 percent. This limitation is particularly important in light of the finding that up to a third of breast cancers detected by screening mammography are smaller than 10 mm. Prognosis depends on early detection of the primary tumor. Spread of a cancer beyond the primary site occurs in approximately 20-30 percent of tumors 15 mm or less in size. However, as tumor size grows beyond 15 mm, there is an increasing incidence of node positive disease, with approximately 40 percent of patients having positive nodes for breast tumors 2 cm in diameter. Hence, for a nuclear medicine technique to be of value in the primary diagnosis of breast cancer, it must be able to reliably detect tumors that are less than 15 mm in diameter. The failure of conventional scintimammography to meet this limit led to its abandonment as a useful technique in the United States.

In an attempt to overcome the limitation of conventional scintimammography, several small field-of-view gamma cameras have been developed that permit the breast to be imaging in a similar manner and orientation to conventional mammography. One commercial system for single photon imaging that is currently available is that manufactured by Dilon Technologies of Newport News, Va. Using a small detector and compression paddle, they reported a sensitivity of 67 percent for the detection of sub-10 mm lesions.

These systems employ a small gamma-ray camera that is attached to a mammography unit or to a stand-alone system in such a way that the gamma-ray camera is proximate to or in direct contact with a breast compression system. The system includes two identical opposing CZT detectors and performs planar imaging of the breast under compression. Recent clinical studies with the dual-head system have shown an increase in sensitivity to nearly 90 percent for lesions less than 10 mm.

Despite this improved percentage of success, the failure to identify lesions of any size can have significant consequences. Accordingly, it would be desirable to have a system and method to provide additional information to aid in the process of diagnosis, analysis, and treatment planning.

To overcome the aforementioned deficiencies, a molecular breast imaging ("MBI") system was introduced by providing a system for performing quantitative tumor analysis using information acquired with a dual-headed molecular breast imaging system. Specifically, the MBI system utilize the information available in planar dedicated breast imaging to provide previously unavailable information sets to aid in the diagnosis and biopsy of the site. MBI system can accurately determine the size, depth to the collimator, and relative tracer uptake of a tumor. The MBI system employs two small opposing gamma camera detectors. The breast is compressed between the two gamma cameras and radiation emitted by single-photon radiopharmaceuticals, such as Tc-99m sestamibi, is detected by collimation.

Although multiple possible radiotracers are available for breast imaging with MBI, Tc-99m Sestamibi is FDA approved and is the most widely used tracer. Because MBI involves intravenous injections of the radiotracer, it poses a very different type of radiation risk than x-ray mammography. The radiotracer distributes throughout the body, exposing many organs and tissues to radiation, in contrast to mammography, in which the only organ affected by radiation is the breast. So, even though the radiation dose to breast tissue is low with MBI, the dose to other organs, and the consequential radiation risk, can be higher than desired. Current techniques employ an administered dose of 20-30 mCi Tc-99m sestamibi that results in an effective dose to the body of 6.5-10 millisievert (mSv). This is about 2-3 times the annual exposure from natural background radiation in the U.S. (~3 mSv) and is ~7-10 times that of mammography. Thus, there is a need to substantially reduce the radiation dose from MBI (by a factor of 5-10), so that this technology can compete against mammography in a screening environment. However simply reducing the administered dose of Tc-99m sestamibi is not possible as the increased noise level in the resulting images significantly degrades image quality. Hence, both hardware and software enhancements need to be made to the technology in order to achieve this level of dose reduction while maintaining image quality.

With that said, the MBI system has been shown to have a relatively high sensitivity (>90%) for the detection of sub-10 mm lesions. In addition, studies have shown that MBI detected 3 times as many cancers as digital and analog mammography in asymptomatic women at increased risk of breast cancer. More recent studies have found the sensitivity of MBI to be comparable to that of MRI. Hence, MBI appears to be a very attractive alternative to mammography, particularly in women at increased risk of breast cancer and in women with dense breast tissue on this mammogram.

Accordingly, it would be desirable to have a method that can obtain satisfactory images with MBI for both the diagnosis and screening of breast cancer by using a reduced radiotracer dose.

SUMMARY OF THE INVENTION

The present invention overcomes the aforementioned drawbacks by providing a system and method for securing MBI images at a substantially reduced dose of radiotracer by increasing the range of photon energies included in the acquired data used to create images.

In accordance with one aspect of the invention, a method is disclosed for imaging a region of interest ("ROI") including a breast having received a dose of radionuclide using an imaging system including at least two gamma detectors arranged in opposition with the ROI arranged therebetween. The method includes acquiring imaging data of the ROI using the at least two gamma detectors and segregating the imaging data into a plurality of subset of data by using a relative energy associated with the imaging data with respect to a photopeak. The method also includes generating a plurality of images using the subsets of data, wherein the plurality of images include a primary image corresponding to subsets of data having energy including the photopeak and multiple scatter images corresponding to subsets of data having energy below and not including the photopeak. The method further includes processing each of the plurality of images using energy information associated with each of the plurality of images and combining the processed plurality of images to form a composite image of the ROI.

In accordance with another aspect of the invention, a method is disclosed for imaging a region of interest ("ROI") including a breast having received a dose of radionuclide using an imaging system including at least two gamma detectors arranged in opposition with the ROI arranged therebetween. The method includes acquiring imaging data of the ROI using the at least two gamma detector, analyzing the imaging data with respect to an energy characteristic and dividing the imaging data into subsets of data based the analysis. The method also includes generating a plurality of images using the subsets of data, wherein the plurality of images include a primary image corresponding to subsets of data having energy including the energy characteristic and multiple secondary images corresponding to subsets of data having energy not including the energy characteristic. The method further includes processing each of the plurality of images using energy information associated with each of the plurality of images and combining the processed plurality of images to form a composite image of the ROI.

In accordance with yet another aspect of the invention, a nuclear imaging system is disclosed that includes at least two gamma cameras in spaced arrangement such that a region for receiving a portion of a subject is defined therebetween. The system also includes a compression mechanism capable of moving at least one of the gamma cameras along an axis and configured to compress the portion of the subject to a selected thickness and a processor configured to access a computer readable storage medium having stored thereon instructions. When the instructions are executed by the processor, the processor is caused to utilize the at least two gamma cameras to detect photons emitted from the portion of the subject in the region between the at least two gamma cameras in order to collect imaging data. The processor is further caused to segregate the imaging data into a plurality of subset of data by using a relative energy associated with the imaging data with respect to a photopeak. The processor is also caused to generate a plurality of images using the subsets of data, wherein the plurality of images include a primary image corresponding to subsets of data having energy including the photopeak and multiple scatter images corresponding to subsets of data having energy below and not including the photopeak. The processor is also caused to process each of the plurality of images using energy information associated with each of the plurality of images and combine the processed plurality of images to form a composite image of the portion of the subject.

In accordance with still another aspect of the invention, a nuclear imaging system is disclosed that includes at least two gamma cameras in spaced arrangement such that a region for receiving a portion of a subject is defined therebetween. The system also includes a compression mechanism capable of moving at least one of the gamma cameras along an axis and configured to compress the portion of the subject to a selected thickness and a processor configured to access a computer readable storage medium having stored thereon instructions. When the instructions are executed by the processor, the processor is caused to utilize the at least two gamma cameras to detect photons emitted from the portion of the subject in the region between the at least two gamma cameras in order to collect imaging data. The processor is further caused to analyze the imaging data with respect to an energy characteristic and divide the imaging data into subsets of data based the analyzing. The processor is also caused to generate a plurality of images using the subsets of data, wherein the plurality of images include a primary image corresponding to subsets of data having energy including the energy characteristic and multiple secondary images corresponding to subsets of data having energy not including the energy characteristic. Also, the processor is caused to combine the processed plurality of images to form a composite image of the portion of the subject.

Various other features of the present invention will be made apparent from the following detailed description and the drawings.

DETAILED DESCRIPTION OF THE INVENTION

Conventionally, nuclear medicine gamma cameras employ energy windows centered on the primary gamma ray energy emitted by the radioisotope being detected. For example, with Tc-99m, a 20 percent energy window (from 126-154 keV) is centered on the 140 keV gamma rays. At lower energies, scatter within the patient and the gamma camera degrade image quality and these events are not considered useful.

In molecular breast imaging, the present invention recognizes that useful clinical images can be obtained at energies below the primary gamma ray energy. With this recognition in place, the present invention provides a method for extracting useful clinical information and images at these lower energies. By doing so the present invention improves image quality and can use this additional information to reduce the scan time or reduce patient radiation dose.

Figure 1:
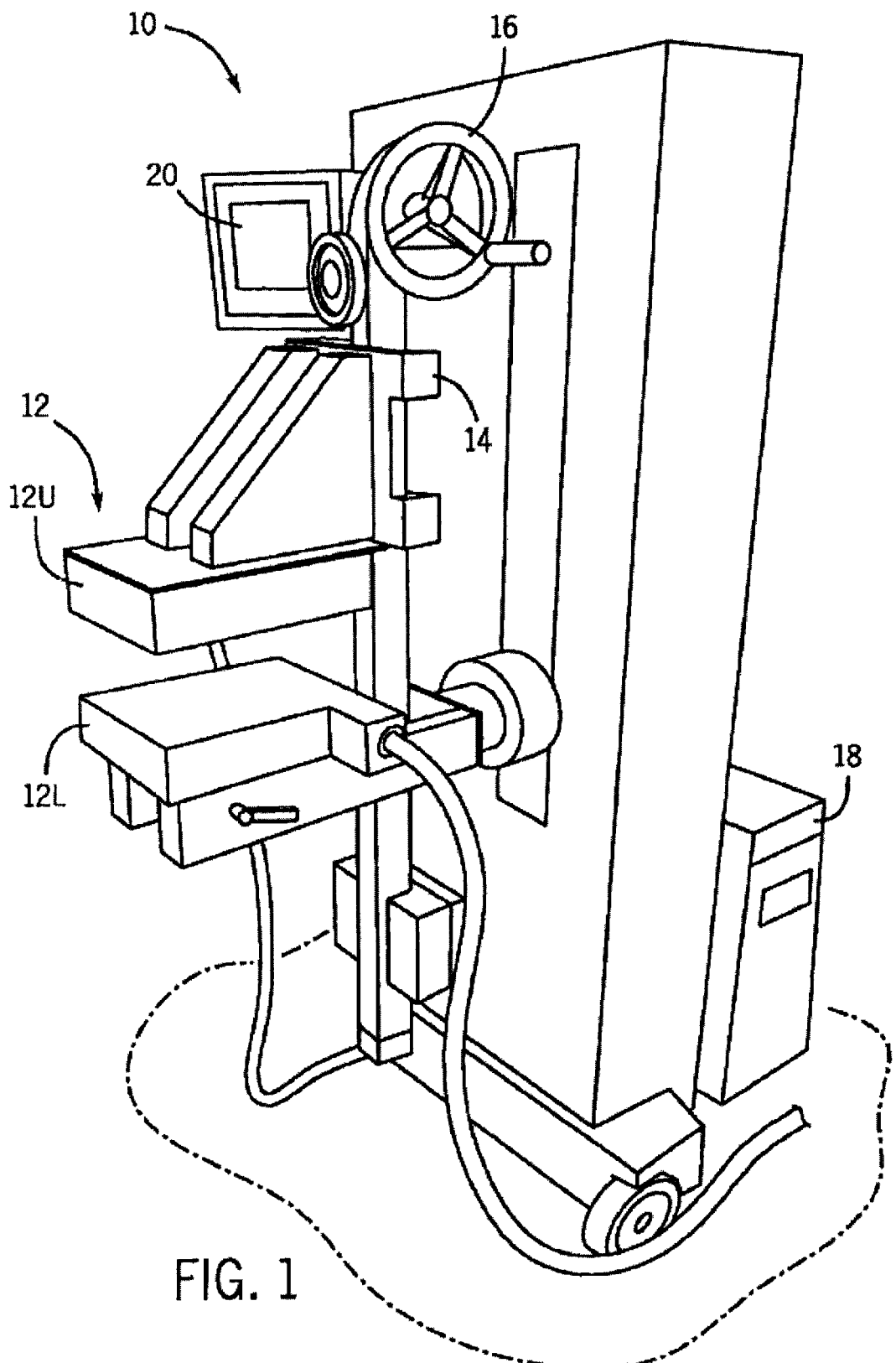
FIG. 1 is an perspective view of a molecular breast imaging system for use with the present invention.

Referring to FIG. 1, a molecular breast imaging (MBI) system 10 includes two opposing CZT detectors (detector heads) 12. In particular, the detector heads 12 include an upper detector head 12U and a lower detector head 12L. Each detector head 12U, 12L is, for example, 20 cm by 16 cm in size and mounted on a modified upright type mammographic gantry 14. In accordance with one embodiment, the detector heads 12 are LumaGEM 3200S high-performance, solid-state cameras from Gamma Medica having a pixel size of 1.6 mm. LumaGEM is a trademark of Gamma Medica, Inc. Corporation of California.

The relative position of the detector heads 12 can be adjusted using a user control 16. Specifically, the detector head assemblies 12 are, preferably, designed to serve as a compression mechanism. Accordingly, this system configuration reduces the maximum distance between any lesion in the breast and either detector head 12 to one-half of the total breast thickness, potentially increasing detection of small lesions without additional imaging time or dose. The MBI system 10 includes a processor 18 for processing the signals acquired by the detector heads 12 to produce an image, which may be displayed on an associated display 20.

Conventional nuclear imaging employs energy windows centered on the photopeak. At lower energies, image quality is significantly degraded and it is widely accepted that little useful information can be obtained from sampling at these energies. Empirical evidence has demonstrated that images acquired below the primary photopeak of Tc-99m at 140 kev are significantly degraded compared to the primary photopeak image, and consequently are usually excluded from further analysis.

However, with semiconductor detectors such as cadmium zinc telluride (CZT), the excellent energy resolution of these devices, coupled with the pixelated nature of these detectors opens up the possibility of extracting information at energies below the photopeak. CZT detectors, which are commonly employed in many nuclear medicine applications, are known to have tailing effects. Due to the low transport properties of carriers, electron-hole pairs generated in a CZT sensor by gamma radiation cannot be completely collected in each electrode. Eventually, this problem leads to a significant distortion of the spectrum and tail effect at the low energy side of the full energy peak. Consequently a standard 20 percent energy window centered on the photopeak may exclude many useful events. A CZT-based gamma camera system employed with an energy resolution of approximately 4 percent (compared to 10 percent for conventional gamma camera) and a pixel size of approximately 1.6 mm, shows that there is considerably less degradation in image quality at lower energies and hence, using the present invention, it is clear that additional, clinically-useful, diagnostic information can be acquired without increasing the dose to the patient.

Figure 2:
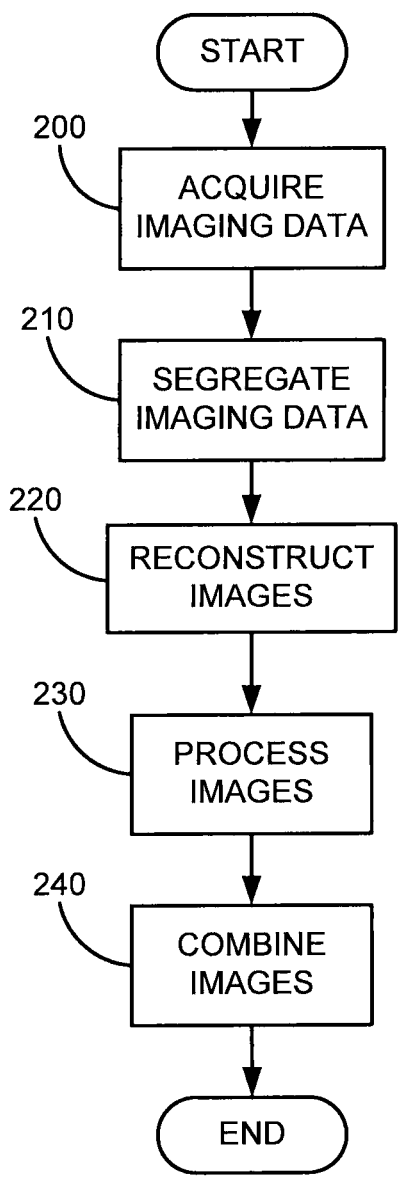
FIG. 2 is a flow chart setting forth the steps for a method of imaging a region of interest (ROI) using the imaging system in FIG. 1.

Referring to FIGS. 1 and 2, a process in accordance with the present invention begins at process block 200 acquiring imaging data from a region of interest ("ROI"), for example, a breast. A routine procedure prior to process block 200 can be taken, such as injecting a subject with a dose of radionuclide, such as Tc-99m sestamibi, positioning the subject for imaging, and adjusting the detector heads 12 using the user control 16 to lightly compress the breast between the upper detector head 12U and lower detector head 12L to improve image contrast and reduce motion artifacts.

Once the positioning and preparation procedure is finished, images data can be acquire at process block 200. Image data is acquired by each detector head 12U, 12L of each breast at multiple views. For example, an image may be acquired in craniocaudal (CC) and mediolateral oblique (MLO) positions for 10 minutes per view. Furthermore, it is contemplated that imaging may be performed at multiple directions using both the craniocaudal and mediolateral oblique breast views to obtain a three-dimensional estimate of tumor size.

At each view of the breast, imaging data is acquired, for example, substantially simultaneously, by the upper detector head 12U and the lower detector head 12L. Each of the acquired imaging data sets is associated with a relative energy. After the imaging data is acquired at process block 200, the imaging data is segregated into a plurality of subsets of data at process block 210, for example, using a relative energy associated with the imaging data with respect to a photoelectric absorption peak, or photopeak. In this case, the relative energy associated with the imaging data may be a photopeak that can be discerned across the imaging data. After segregation, a plurality of images is reconstructed at process block 220 using the subsets of data. These reconstructed images include a primary image and multiple scatter images. The primary image corresponds to subsets of data having energy including the photopeak. The multiple scatter images correspond to subsets of imaging data having energy below and not including the photopeak. After the plurality of images are reconstructed, each of the plurality of images is processed using energy information associated with each of the plurality of images at process block 230. This step of processing may include multiple sub-steps and will be described in detail below. The processed images may, if desired, be combined at block 240, to form a composite image for each view of the breast.

To determine the value of using lower energy photons, two scatter correction methods, the triple energy window (TEW) approach and transmission-dependent convolution subtraction (TDCS), as applied to MBI were evaluated. First, several Monte Carlo models were created to simulate a variety of breast lesions typically encountered in MBI. From the models, simulated images were created and processed using two common scatter correction techniques: Triple Energy Window (TEW) and Transmission-Dependent Convolution Subtraction (TDCS). The resulting images were analyzed using a Channelized Hotelling Observer (CHO) to determine the correction method and energy window best suited for MBI. In addition to the evaluation of these scatter correction methods, a wide energy window—from 110 keV-154 keV was evaluated in clinical studies.

Monte Carlo Model

The Monte Carlo model was created using Monte Carlo N-Particle Transport Code 5 (MCNP5, Los Alamos National Laboratory) by modifying a previously described model of the MBI system. The model retained the patient torso anatomy, including a heart, liver, and compressed breast of the original model. An upper head detector was added to better represent the actual MBI gantry, and the modeled collimator was changed to match the tungsten collimator described above. The number of particles simulated was held constant to produce a count rate that was statistically equivalent to patient data as previously published, taking into account the increased sensitivity with the newly-modeled collimator. This was considered a model at "100 percent" time and dose; models with 20 percent, 40 percent, 60 percent, and 80 percent the count rate were also generated to represent images acquired in less time and/or with decreased dose. The only variables between models were lesion characteristics: depth in the breast tissue (1, 2, or 3 cm from the lower detector), spherical diameter (5, 7.5 or 10 mm), and distance from the chest wall (near the chest wall, at the center of the breast, or near the nipple). The output from the Monte Carlo models was then processed to reflect the energy tailing and blurring that occur as a result of the CZT detectors used in MBI. The model of the tailing was based on an approximate solution of the Schockley-Ramo theorem. The charge induced at the CZT anode, $\Delta Qk$, was expressed as:

$$\Delta Q_k = \frac{\lambda_e^* \square N_0 \square q}{\tau_a} \square \frac{\exp\left(\frac{x_0 - d}{\lambda_e}\right)}{1 - \exp\left(-\frac{d}{\tau_a}\right)} \square \left(1 - \exp\left(\frac{x_0 - d}{\lambda_e^*}\right)\right); \quad \text{eqn. 1}$$

for an energy deposition $N_0 \square q$ at a location $x_0$ in the CZT detector with a depth d in an electric field E. The values for the electron mobility ($\mu_e$) and lifetime ($\tau_e$) were obtained from the manufacturer's CZT material properties report 18. $\tau_a$ is the decay constant of the weighting function, found as the value that provided the best fit between the equation and the model's weighting function. The energy spectrum was then blurred with a Gaussian kernel such that the energy resolution was that of the MBI system (3.8 percent).

Scatter Correction

Two common scatter correction methods—Triple Energy Window (TEW) and Transmission-Dependent Convolution Subtraction (TDCS)—were applied to the images generated by the Monte Carlo models. In each method, the scatter component is estimated and subtracted from the original image, such that the remaining image represents a theoretically scatter-free image. TDCS necessitates that the geometric mean be taken to eliminate depth dependence. For that reason, the geometric mean was also taken of the uncorrected (original) and TEW corrected images for comparison purposes. Additionally, this is reflective of the post-processing that would need to be done to combine the dual-head images.

Triple Energy Window

The TEW method was first proposed by Ogawa et al at Ogawa, K., Harata, Y., Ichihara, T., Kubo, A., Hashimoto, S. "A practical method for position dependent Compton-scatter correction in single photon emission CT." IEEE T. Med. Imaging, 10: 408-412 (1991), which is incorporated herein by reference. Two small sub-windows adjacent to the main photopeak window are used to form a trapezoidal approximation of the scatter in the main energy window. That is then subtracted from the main window. The remaining non-scatter (primary) count rate, $C_{prim}$, is defined as:

$$C_{prim} = C_{total} - \left[\frac{C_{left}}{W_S} + \frac{C_{right}}{W_S}\right]\frac{W_M}{2}. \quad \text{eqn. 3}$$

The value for Cright was 0, as was decided upon by Ogawa et al. This was appropriate for MBI, as the count rate at the main energy window's upper limit (155 keV) is negligible. Because the energy spectra differ between the CZT used in MBI and traditional NaI detectors, the lower limit for the main window and its adjacent sub-window were varied from 125 to 90 keV. The size of the sub-windows was 3 keV, as used by Ogawa et al. Hence, for example, for a primary window 110-154 keV, the lower sub-window was set at 106-109 keV.

Transmission-Dependent Convolution Subtraction

TDCS, developed by Meikle, Meikle, Steven R., Hutton, Brian F., Bailey, Dale L. "A transmission-dependent method for scatter correction in SPECT." J. Nucl. Med, 35: 360-367 (1994), which is incorporated herein by reference, is a method in which the scatter image is estimated by convolving the original photopeak image, gobs, with a scatter function, s, and then scaling it by a matrix of scatter fractions, kT, which are determined from transmission data for each pixel. This is then subtracted from the original image to obtain the scatter-free image:

$$g(x,y) = g_{obs}(x,y) - k_T(g_{obs}(x,y) \otimes s) \quad \text{eqn. 4.}$$

The scatter matrix, kT, and the scatter function, s, should be known. The scatter matrix, kT, is related to the transmission data by the equation:

$$k_T(x, y) = 1 - \frac{1}{A - Bt(x, y)^{\beta/2}}; \quad \text{eqn. 5}$$

where $k_T(x,y)$ is the scatter fraction for a given pixel, and t(x,y) is the transmission factor defined as $t(x,y) = e^{ud}$, where u is the attenuation coefficient and d is the depth of material. Coefficients A, B, and beta are found by plotting $k_T(x,y)$ versus t(x,y) and fitting the above equation.

For the purposes of MBI, the attenuation coefficient u can be assumed to be one of two values, depending whether the tissue at a given pixel is air or breast. It can be assumed that all areas of air had zero attenuation. The attenuation of breast can be found by using the elemental compositions of adipose and glandular tissue found by known mechanisms for input to the NIST photon cross sections database, XCOM23. Despite variations in breast composition, each yields the same attenuation value for 140 keV photons: 0.151 cm²/g.

The scatter fraction $k_T(x,y)$ in the medium varies by source activity distribution and thickness of material. This was found by modeling two different distributions of activity in varying thicknesses of material: (1) the activity was uniformly distributed throughout the medium, and (2) the activity was restricted to a plane parallel to the detector through the center of the medium. The scatter fraction of each distribution was determined for a range of depths from 0.5 to 8 cm, and the mean of the two was used in the fitting of coefficients A, B, and beta for each energy window investigated. The scatter function, s, is classically defined as the mono exponential "wings" observed in a point spread function:

$$s(r) = a \exp(-br) \quad \text{eqn. 6;}$$

where s(r) is the counts at a given radius r from the point source, and coefficients a and b were found from fitting the wings of s(r) vs r for each energy window.

Last, it has been suggested that several iterations of TDCS could improve its performance. This has been investigated and it was found that the above equation for $k_T$ is appropriate for a single iteration of TDCS, but adjustments are desirable for subsequent iterations. The following equation was then used after the first iteration:

$$k_T(x,y)=A-Bt(x,y)^{\beta/2}-1 \qquad \text{eqn. 7.}$$

Again, energy windows with an upper limit of 155 keV and lower limit ranging from 90 to 125 keV were investigated.

Channelized Hotelling Observer

With the different lesion characteristics and energy windows, a total dataset of 4860 uncorrected images was created, and each image was processed separately by TEW and TDCS as described. A paired signal-absent dataset was created by removing the photons that originated from the lesions in the Monte Carlo model outputs. Additionally, the images were divided into datasets according to the lower energy window limits to assess the effect of energy window selection on detectability.

Due to the expense, time, and volume of images in the study, a human observer study was not conducted. Rather, a channelized Hotelling observer with Laguerre-Gauss channels (LG-CHO) was used to evaluate the change in lesion detectability with different scatter correction methods and energy windows. LG-CHO have been showed as an accurate prediction of human performance in signal-detection tasks. For this study, ten Laguerre-Gaussian channels were used, and their lotions and sizes were adjusted according to the characteristics of each lesion. ROCKIT, a program developed by Metz et al., was used to perform the receiver operating characteristic (ROC) curve analysis on the test statistics of the LG-CHO model. In particular, the area under the ROC curve, Az, was used as the definitive index of performance.

Optimization of Energy Window Setting

A number of methods were studied to improve utilization of gamma rays detected at energies lower than the photopeak of Tc-99m (140 keV). The most simplistic was to employ a wider energy window. Patient images acquired using a standard energy window (from 126 keV-154 keV), and a asymmetrical wide window (from 110 keV-154 keV) using the conventional hexagonal hole collimator and an administered dose of 20 mCi were compared. The wider window resulted in a 1.5-2.0 gain in sensitivity with minimal loss of contrast. Some increase in scatter was noted in some images close to the chest wall. This was more pronounced in images from the upper detector than from the lower detector.

Scatter Correction

The two scatter correction methods, TEW and TDCS, each showed improvement in detectability over the uncorrected images according to the area under the ROC curve (Az). In particular, in 100 percent images, the original uncorrected images produced an Az of 0.9533 with a 95 percent confidence interval (CI) of 0.9435 to 0.9616. This was improved to 0.9821 (95 percent CI: 0.9760 to 0.9868) with TDCS and to 0.9976 (95 percent CI: 0.9939 to 0.9991) with TEW. The utility of the scatter correction methods at greater noise was investigated by using the 20, 40, 60, and 80 percent images. Again, improvement was found over the original uncorrected images for both TDCS and TEW, with TEW being superior in each instance.

Energy Window

To assess the optimal energy window, the data set of images was subdivided into 2 keV energy bins according to the lower limit of the main energy window. That is, images generated with energy windows of 90-155 keV and 91-155 keV were binned together, 92-155 keV and 93-155 keV were binned together, and so on. ROC curves were generated as they were for the general analysis done. The Az values were recorded and plotted against the lower energy window limits, being 90.5 keV, 92.5 keV, 94.5 keV, and so on.

The trend across varying energy windows varies according to the correction method used. The original, uncorrected images showed an overall decrease in Az as the energy window was widened. The greatest Az values occurred when the lower energy window limit is at least 115 keV. Az decreased to a slightly lower constant level as the energy window was widened to about 103 keV. There was then a noticeable decline in Az as the energy window was widened further to about 95 keV, after which Az slightly increased just above a lower limit of 90 keV. The TEW correction method, which showed the greatest overall Az values as shown in the previous section, again showed the greatest Az value, with a peak just above 100 keV and another just above 110 keV. The trend across the energy windows showed greater fluctuation in Az values, making it difficult to discern a trend. The TDCS correction method had a trend of a stable, constant Az value across all energy windows, which was not as great as that with TEW at some energy windows, but was consistently greater than uncorrected alone. The TEW resulted in considerable increase in the noise level in the correction image, relative to the TDCS algorithm.

Though TEW showed the greatest Az, its variability across the energy spectrum and poor quality visually make TEW undesirable for MBI. TDCS is better suited as it shows improved Az with consistency and quality. When TEW is used, it is potentially favorable to be done on a neighborhood basis, rather than pixel-by-pixel. When TDCS is employed, it is possible to reduce the dose to 60 percent with comparable detectability to a 100 percent original image, as the 60 percent TDCS lower bound and 100 percent original upper bound of the CI are nearly equal.

The wide energy window of 110-154 keV yields a 1.44 gain in sensitivity. The 105-154 energy window gave a further 12 percent increase in sensitivity, and compared to the standard energy window had an overall gain 1.62. However use of this wider energy window needs to be accompanied by the TDCS algorithm to retain lesion detectability.

Thus, the use of a wide energy window coupled with the implementation of scatter correction techniques allows for a significant gain in system sensitivity, which can be translated to a lower administered dose of radiation to the patient. With this analysis as the backdrop, a variety of methods are contemplated for creating and using the scatter images. For example, referring to FIG. 3, one such process begins at process block 300 by setting a plurality of energy windows. The plurality of energy windows include a primary energy window covering the photopeak and a plurality of scatter energy windows below and not covering the backscatter peak. After energy windows are set, imaging data is acquired at each energy window at process block 310 and 320 and decision block 330, until all the imaging data at each energy window are required.

For example, for the case of using Tc-99m, this may involve acquiring imaging data information from approximately 80 kev to approximately 155 kev. Six energy windows can be created over the following energy ranges:

Primary energy window (P)=125-155 kev;
Scatter energy window 1 (S1)=115-125 kev;
Scatter energy window 1 (S2)=105-115 kev;
Scatter energy window 1 (S3)=95-105 kev;

Scatter energy window 1 (S4)=85-95 kev; and

Scatter energy window 1 (S5)=75-85 kev.

A plurality of images are reconstructed at process block 340 using the imaging data at each energy window, respectively. These reconstructed images include a primary image and multiple scatter images. The primary image corresponds to the imaging data acquired at the primary energy window. The multiple scatter images correspond to imaging data acquired at the scatter energy windows. After the plurality of images are reconstructed, each of the plurality of images is processed, as will be described, using energy information associated with each of the plurality of images at process block 350. The images may, if desired, then be combined at block 360, to form a composite image for each view of the breast.

Figure 4:
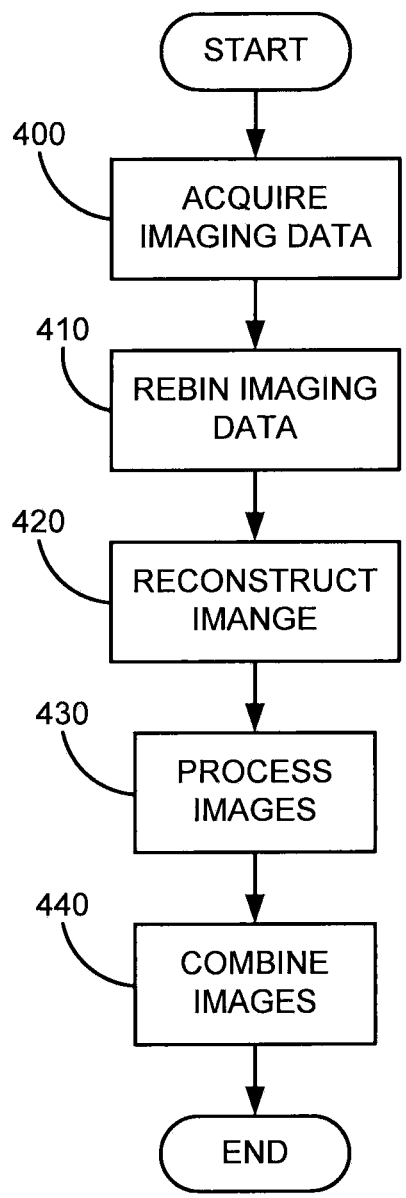
FIG. 4 is a flow chart setting forth the steps of a method of imaging a ROI in FIG. 2 using a rebinning method.

As stated, a variety of methods are contemplated for creating and using the scatter images. Referring to FIG. 4, another process begins at process block 400 by acquiring imaging data in list mode. Each of the acquired imaging data sets is associated with a relative energy bin that is included in a list of energy bin. Thus, the acquired imaging data can be rebinned into a plurality subsets of data at process block 410 using the relative energy bin associated with the imaging data with respect to a photopeak. At block 420, a plurality of images are generated using the subsets of data. Again, these reconstructed images include a primary image and multiple scatter images. The primary image is corresponding to subsets of imaging data having energy bin including the photopeak. The multiple scatter images are corresponding to subsets of imaging data having energy bin below and not including the photopeak. After the plurality of images are reconstructed, each of the plurality of images is processed using energy information associated with each of the plurality of images at process block 430 and, can be, combined at block 440 to form a composite image for each view of the breast.

Figure 3:
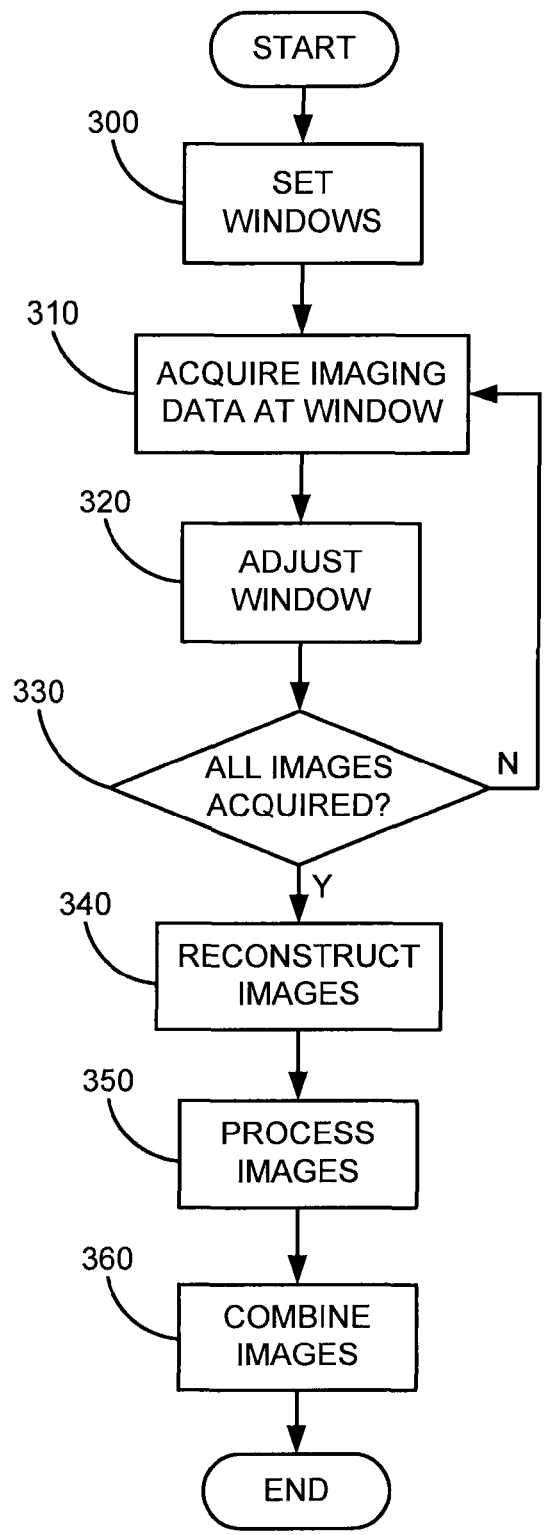
FIG. 3 is a flow chart setting forth the steps of a method of imaging a ROI in FIG. 2 using a windowing method.
Figure 5:
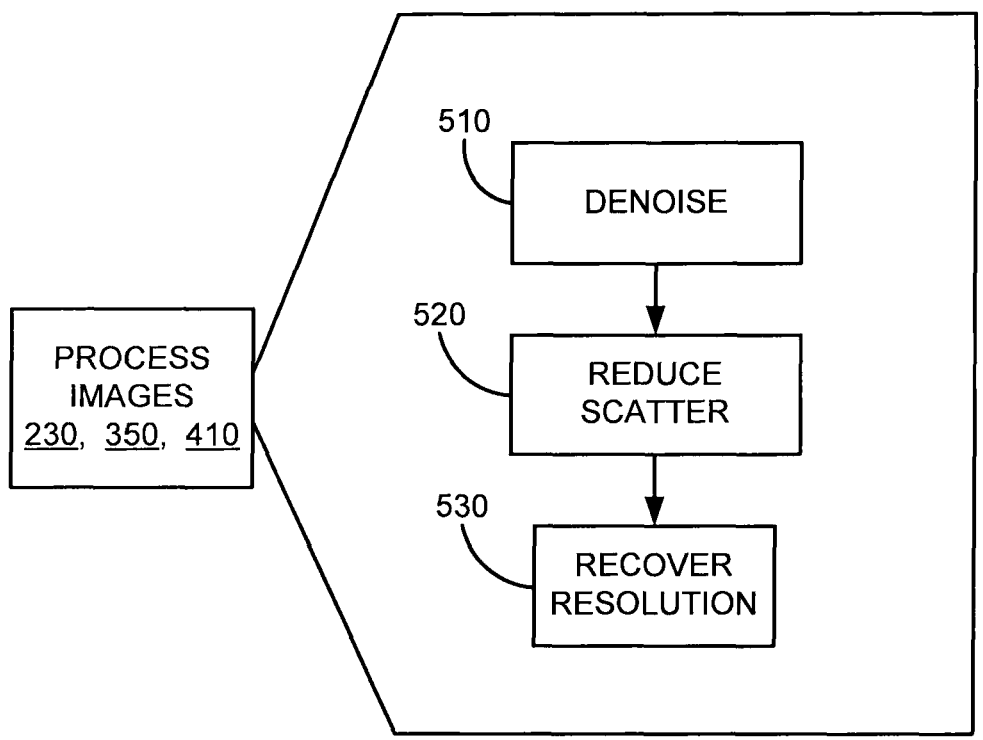
FIG. 5 is a flow chart setting forth the steps for processing reconstructed images in FIG. 2, FIG. 3, and FIG. 4.

Referring to FIG. 5, process block 230 in FIG. 2, process block 350 in FIG. 3, and process block 430 in FIG. 4 may include denoising the primary image and each of the scatter images at process block 510, reducing scatter at process block 520, and recovering resolution in each of the scatter images at block 530.

At block 510, denoising can be performed to reduce the noise content, particularly of the lower energy scatter images. For example, one desirable filter for this step is a non-local means (NLM) filter. This filter is based on self-similarity in the image and, for each pixel, calculates a filtered value based on a weighted average of other pixels within a large search region, with the weights determined by how similar the spatial neighborhoods of the two pixels are.

Since the imaging data has Poisson noise statistics, but the NLM filter is based on Gaussian noise statistics, the Anscombe transform (output=2 sqrt (input+3/8)) can be applied to the image at block 510 to reduce noise. This is a statistical tool to convert Poisson distributed data to data with an approximately normal distribution with a constant variance. This transformation is considered valid when the mean value of the Poisson data is greater than, for example, 20. Although this is not necessarily the case here in the background regions of low-dose scans, filtering the transformed data is superior to filtering the original data even in this case.

Referring to process block 520, are a number of methods for scatter correction in nuclear medicine are suitable within the context of the present invention. For example, considering scatter energy windows S to S7, a $7^{th}$ energy window can be acquired using an energy window below Scatter energy window S5. This image would be denoised leaving only the low and mid-range frequencies present. A fraction of this image is then used to correct for scatter in images S1 to S5. In an alternative configuration of the scatter reduction algorithm, scatter reduction is performed by removing a portion of the low frequency components of each of the images S1 to S5. The precise fractions or amounts to remove is determined by general breast geometries.

At process block 530, a number of resolution recovery algorithms are contemplated within the context of the present invention. For example, images from line or point sources can be used to generate line or point spread functions from each image and, from these, a set of convolution functions can be computed as follows:

$$P*C1=S1; \text{ and}$$

$$P*C2=S2 \ldots P*C3=S3.$$

Since P and S1-S5 are known, and C should vary slowly between C1 and C5, this permits a more robust estimate of the convolution function and how it varies between S1 and S5. This is particularly important as noise present in signals S1-S5, will make reliance on the individual values of C1 to C5 problematic. Deconvolution of each scatter image can be performed using the appropriate inverse function derived from analysis of C1-C5, as follows:

$$SC1=(S1-\epsilon1)*C1^{-1};$$

$$SC2=(S2-\epsilon2)*C2^{-1},$$

where SC is the deconvolved version of S and $\epsilon$ represents the noise in the S signal that will be removed in part a) above. Following deconvolution of S1-S5, the outputs will be summed with P to yield a new composite image.

Within the context of the present invention, this represents just one possible scheme for resolution recovery of the scatter images. A number of possible schemes can be used to perform resolution recovery on these images, including the use of filters designed for restoration purposes (e.g. Metz and Weiner filters). The present invention has been described in accordance with the embodiments shown, and one of ordinary skill in the art will readily recognize that there could be variations to the embodiments, and any variations would be within the spirit and scope of the present invention. Accordingly, many modifications may be made by one of ordinary skill in the art without departing from the spirit and scope of the appended claims.

What is claimed is:

1. A method for imaging a region of interest ("ROI") including a breast that has received a dose of radionuclide with a molecular breast imaging (MBI) system, the method comprising the steps of:
   a) with the use of the at least two gamma detectors of the MBI system, acquiring imaging data representing the ROI that is compressed between said at least two gamma detectors;
   b) segregating the imaging data into a plurality of subsets of data acquired from a plurality of energy windows containing a primary energy window and secondary energy windows,
   a primary energy window from the plurality of energy windows containing a single photopeak;
   energies of each of secondary energy window being lower than any energy from the primary energy window, each secondary energy window not including the single photopeak;
   each subset of data defined according to a corresponding energy window from which data in said subset has been acquired, c) generating a plurality of images using the subsets of data, wherein the plurality of images include
a primary image corresponding to a primary subset of data defined by the primary energy window and
multiple secondary images, each secondary image respectively corresponding to a secondary subset of data defined by a respective secondary energy window;

d) processing each of the plurality of images using energy information associated with each of the plurality of images to form a processed plurality of images, the processed plurality of images including processed secondary images and a processed primary image; and e) recovering imaging counts lost from the primary subset of data due to tailing effects in the at least two gamma detectors
(i) to increase imaging sensitivity of said MBI system as compared with utilizing only the processed primary image
and
(ii) to form a composite image of the ROI that contains information from said multiple secondary images
by adding imaging data represented by processed secondary images to imaging data represented by the processed primary image.

2. The method of claim 1 wherein step a) further includes defining the plurality of energy windows that do not overlap with one another.

3. The method of claim 1, wherein each of the at least two gamma detectors includes semiconductor detectors.

4. The method of claim 1 wherein step d) further includes denoising the primary image and each of the secondary images, and reducing scatter and recovering resolution in each of the secondary images.

5. The method of claim 4, wherein said denoising includes transforming, non-local means filtering of imaging data represented by said plurality of images, and deconvolving each secondary image.

6. The method of 4, wherein said denoising includes performing an Anscombe transforming of imaging data represented by said plurality of images.

7. The method of claim 4, wherein said reducing scatter in each of the secondary images includes removing low frequency components from said each of the secondary images.

8. The method of claim 5, wherein said deconvolving includes deconvolving each of the secondary images by using a convolution function that has been calculated from said each of the secondary images and the primary image.

9. A method for imaging a region of interest ("ROI") including a breast that has received a dose of radionuclide with a molecular breast imaging (MBI) system, the method comprising the steps of:
a) with the use of the at least two gamma detectors of the MBI system, acquiring imaging data representing the ROI that is compressed between said at least two gamma detectors, each said at least two gamma detectors being a semiconductor detector;
b) analyzing the imaging data with respect to a predefined energy;
c) dividing the imaging data into subsets of data based on difference between energy at which said data has been acquired and said predefined energy, wherein the subsets of data include imaging data acquired at energies is selected to compensate loss of imaging data that has occurred due to tailing effects in said at least two gamma detectors;

d) generating a plurality of images using the subsets of data, wherein the plurality of images include
a primary image represented by a subset of data acquired within a primary energy window that contains said predefined energy and
multiple secondary images, each of which is represented by a corresponding subset of data acquired within a corresponding secondary energy window that does not include said predefined energy, a secondary energy window not overlapping with the primary energy window;

e) processing each of the plurality of images using energy information associated with each of the plurality of images to form a plurality of processed images including a processed primary image and processed secondary images; and f) adding imaging data represented by processed secondary images to imaging data represented by the processed primary image to form a composite image of the ROI, said composite image restoring image information lost from the primary subset of data due to said tailing effects.

10. The method of claim 9, wherein the predetermined energy include energy of a single a photopeak.

11. The method of claim 9,
further comprising defining each of said secondary energy windows to contain energies that are lower than energies in the primary energy window.

12. The method of claim 9, wherein step e) further includes denoising the primary image and each of the secondary images, and reducing scatter and recovering resolution in each of the secondary images.

13. The method of claim 12, wherein said denoising includes transforming, non-local means filtering of imaging data represented by said plurality of images, and deconvolving each secondary image.

14. The method of claim 12 wherein said reducing scatter includes using low frequency information from each of the secondary images to correct for scatter in the primary image.

15. The method of claim 12, wherein said recovering resolution includes deconvolving each of the secondary images by using a convolution function that has been calculated from said each of the secondary images and the primary image.

16. A molecular breast imaging (MBI) system comprising:
at least two gamma cameras in spaced arrangement such that a region for receiving a portion of a subject is defined therebetween;
a compression mechanism configured to reposition at least one of the gamma cameras along an axis to compress the portion of the subject between the least two gamma cameras to a selected thickness;
a processor operably connected with a computer readable tangible non-transitory storage medium that has stored thereon instructions, which instructions, when executed by the processor, cause the processor to
a) collect imaging data from the at least two gamma cameras as a result of detection of photons emitted from the portion of the subject that has been compressed in the region between the at least two gamma cameras of the MBI system;
b) segregate the imaging data into a plurality of subsets of data, each subset of data defined according to a corresponding energy windows at which data in said subset has been acquired,
a plurality of energy windows defined with respect to a single photopeak and containing a primary energy window and secondary energy windows, the primary energy window containing said single photopeak, energies within each of said secondary windows being lower than any energy from the primary energy window, each secondary window not including the single photopeak;

c) generate a plurality of images using the subsets of data, wherein the plurality of images include
   (i) a primary image corresponding to a primary subset of data defined by the primary energy window and
   (ii) multiple secondary images, each secondary image respectively corresponding to a secondary subset of data defined by a respective secondary energy window;

d) process each of the plurality of images using energy information associated with each of the plurality of images to form a plurality of processed images including processed secondary images and a processed primary image; and e) add imaging data represented by processed secondary images to imaging data represented by the processed primary image to form a composite image of the ROI to restore image information lost from the primary subset of data due to tailing effects in said at least two gamma cameras.

17. The system of claim 16, wherein each of said at least two gamma cameras includes a semiconductor detector.

18. A molecular breast imaging (MBI) system comprising:
   at least two gamma cameras disposed in parallel and spaced arrangement such that a region for receiving a portion of a subject is defined therebetween;
   a compression mechanism configured to move at least one of the gamma cameras along an axis and to compress the portion of the subject to a selected thickness between said at least two gamma cameras;
   a processor configured to access a computer readable storage medium having stored thereon instructions that, when executed by the processor, cause the processor to:
      with the at least two gamma cameras, collect imaging data by detecting photons emitted from the portion of the subject in the region that has been compressed between the at least two gamma cameras in order to collect imaging data;
      analyze the imaging data with respect to a predetermined energy;
      divide the imaging data into subsets of data based on energy at which said imaging data has been acquired in relation to said predetermined energy, wherein the subsets of data include imaging data that are selected to control tailing effects in said at least two gamma cameras;
      generate a plurality of images using the subsets of data, wherein the plurality of images include
         (i) a primary image corresponding to a subset of data acquired at energies within a primary energy window that includes said predetermined and
         (ii) multiple secondary images corresponding to subsets of data acquired at energies within respectively corresponding secondary energy windows that do not include said predetermined energy; and
      add imaging data represented by the multiple secondary images to imaging data represented by the primary image to form a composite image of said portion of the subject compressed between at least two gamma cameras to restore image information lost from the primary image due to tailing effects in said at least two gamma cameras.

19. The system of claim 18, wherein the predetermined energy includes energy corresponding to a single photopeak.

20. The system of claim 18, wherein each of the at least two gamma cameras includes a semiconductor detector and the processor is further configured to define each of said secondary energy window to not overlap with the primary energy window.

* * * * *